United States Patent [19]

Darras

[11] Patent Number: 4,886,049
[45] Date of Patent: Dec. 12, 1989

[54] MEDICAL INSTRUMENT COVER

[76] Inventor: Robert L. Darras, 2219 Mount Shasta Dr., San Pedro, Calif. 90732

[21] Appl. No.: 195,039

[22] Filed: May 17, 1988

[51] Int. Cl.⁴ ............................................... A61B 1/00
[52] U.S. Cl. ....................................................... 128/4
[58] Field of Search ........................................ 128/4, 6

[56] References Cited

U.S. PATENT DOCUMENTS

| | | | |
|---|---|---|---|
| 3,794,091 | 2/1974 | Ersek et al. | 128/23 X |
| 3,809,072 | 5/1975 | Ersek et al. | 128/23 |
| 4,646,722 | 3/1987 | Silverstein et al. | 128/4 |
| 4,741,326 | 5/1988 | Sidall et al. | 128/4 |
| 4,809,678 | 3/1989 | Klein | 128/4 |

*Primary Examiner*—William H. Grieb
*Attorney, Agent, or Firm*—Spensley Horn Jubas & Lubitz

[57] ABSTRACT

A medical instrument cover having an elongated, generally tubular sheath of an elastomeric material, open at both ends, configured to fit on an endoscope and defining an interior surface. A filament is attached to the interior surface of the sheath and functions to separate the sheath in an elongate direction. In this manner, the sheath is easily removed from the medical instrument which it is covering.

In a second embodiment, two strips of material located generally opposite one another are attached to the interior surface. The sheath is applied to a medical instrument such as an endoscope. When it is desired to remove the sheath from the endoscope, the strips of material are grasped and pulled along the length of the endoscope thus removing the cover from said endoscope.

12 Claims, 1 Drawing Sheet

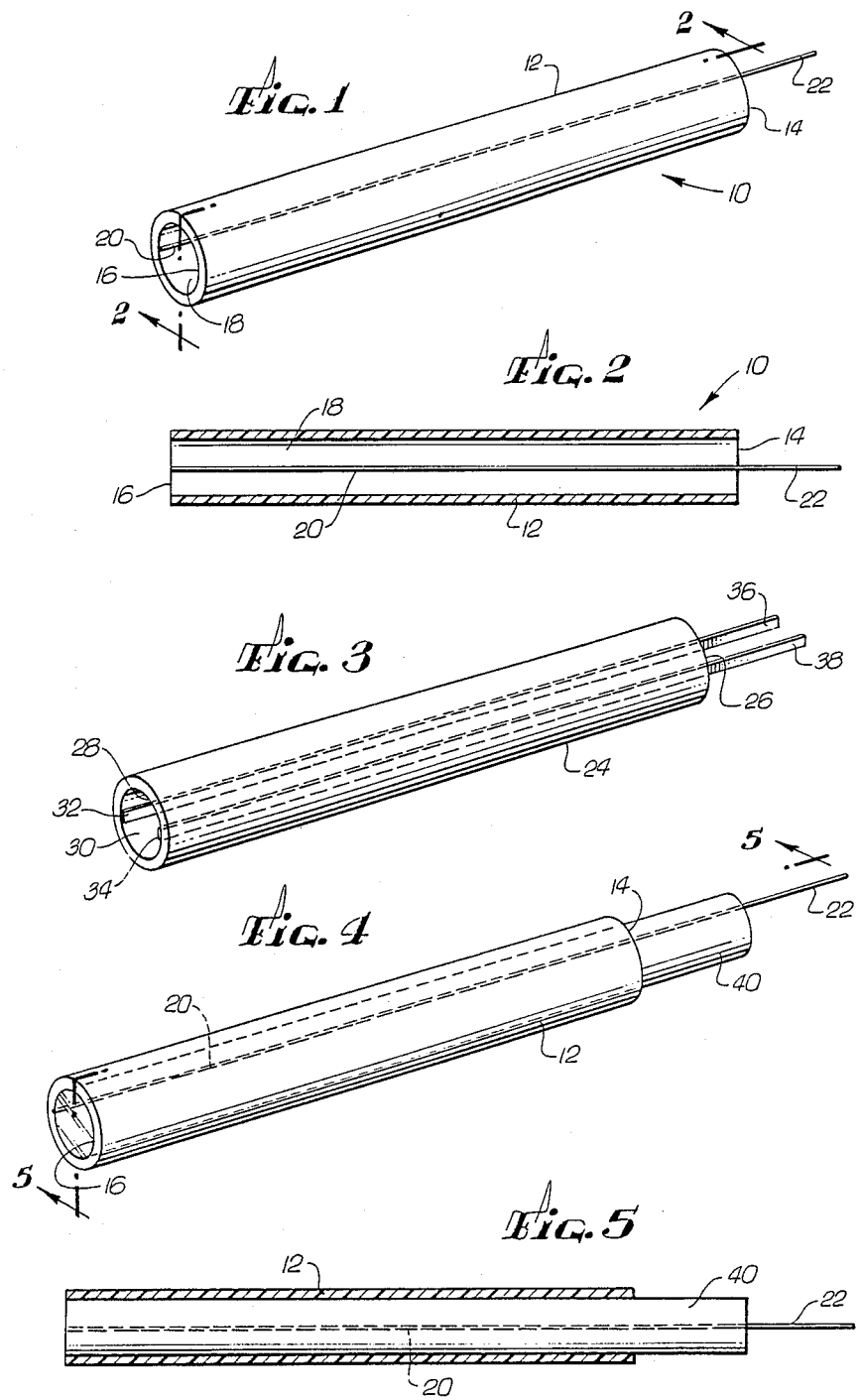

MEDICAL INSTRUMENT COVER

BACKGROUND OF THE INVENTION

The present invention relates to a protective cover for a medical instrument. Specifically, the present invention relates to a cover for a medical instrument which cover can be easily removed from said medical instrument.

Recent years have seen an ever-increasing incidence in the number of new persons suffering from Acquired Immune Deficiency Syndrome (AIDS). Moreover, many health agencies predict that the number of new cases of persons suffering from AIDS will continue to rise in the coming years. Due to the very serious nature of the AIDS disease, much research and effort has been dedicated to finding ways of preventing the spread of this disease.

It is currently believed that AIDS is caused by a virus which is spread from one human to another through the exchange of certain body fluids. For example, it is generally accepted that the AIDS virus can be spread through the exchange of blood, semen, saliva, and the like. Accordingly, much of the research conducted with preventing the spread of the AIDS virus has been directed to preventing the inadvertent exchange of body fluids.

For example, many dentists are now performing dental procedures with protective gloves and face masks to prevent the accidental exchange of blood and/or saliva. Additionally, elaborate means have been developed to protect nurses and lab technicians who deal with human blood from becoming infected with the AIDS virus through the accidental exchange of body fluids.

Endoscopes are medical instruments well known to those skilled in the art. The term endoscope generally refers to an instrument for visualizing the interior of a hollow organ such as the colon or the urethra. A variety of medical instruments fall within the scope of the term "endoscope". For example, flexible endoscopes include upper G.I. fiberscopes, sigmoidoscopes, duodenoscopes or colonoscopes. As the name implies, sigmoidoscopes, duodenoscopes and colonoscopes are employed to visualize areas of the colon or intestine. Endoscopes generally comprise some type of fiberoptic system in a flexible covering. Due to the expensive nature of an endoscope, it is not possible to merely discard an endoscope after use. Accordingly, it is necessary to thoroughly clean and sterilize an endoscope between uses to ensure that body fluids such as blood and the like are not transmitted from one patient to another through the use of a common endoscope.

Unfortunately, the ability to thoroughly clean and effectively sterilize an endoscope is largely dependent upon the skill and care of the person in charge of cleaning and sterilizing the endoscope. The cleaning and sterilization of such endoscopes can be a time consuming and tedious job. Due to the difficulty of cleaning and sterilizing the endoscopes it is believed that there may be occasions when the endoscopes are not thoroughly cleaned and sterilized between uses and that transfer of a virus, such as the AIDS virus, may be possible.

SUMMARY OF THE INVENTION

Accordingly, it is desirable to provide means for simplifying the cleaning and sterilization step of endoscopes and similar medical instruments and to prevent the potential spread of the AIDS virus from one patient to another due to ineffective cleaning and sterilization of such instruments. It is to this goal that the present invention is directed.

These and other goals are achieved by employing a cover for a medical instrument which cover comprises an elongate generally tubular sheath of an elastomeric material such as natural or synthetic rubber or the like. The generally tubular sheath is open at both ends and defines an interior surface. The sheath is adapted to fit snugly about a medical instrument such as, for example, an endoscope. The sheath further comprises means for removing the sheath from the medical instrument.

In another aspect, the present invention concerns a method of employing a medical instrument such as an endoscope. The method involves providing an endoscope which is covered with an elongate generally tubular sheath of an elastomeric material. The sheath is open at both ends and defines an interior surface. The sheath is adapted to fit snugly about a medical instrument such as, for example, an endoscope. The sheath further comprises means for removing the sheath from the endoscope. After the endoscope is employed in a medical procedure, the sheath can be removed by employing the means for removing the sheath.

BRIEF DESCRIPTION OF THE DRAWINGS

FIG. 1 illustrates a perspective view of a first embodiment of the medical instrument cover according to the present invention.

FIG. 2 illustrates a cross-sectional view taken along line 2—2 of FIG. 1.

FIG. 3 illustrates a perspective view of a second embodiment of the medical instrument cover according to the present invention.

FIG. 4 illustrates a perspective view of the medical instrument cover of FIG. 1 shown in place on an endoscope.

FIG. 5 illustrates a cross-sectional view taken along line 5—5 of FIG. 4.

DETAILED DESCRIPTION OF THE ILLUSTRATED EMBODIMENT

In one aspect, the present invention relates to a medical instrument cover. The medical instrument cover of the present invention comprises an elongate generally tubular sheath of an elastomeric material. The sheath is open at both ends and defines an interior surface. The sheath is adapted to fit snugly about a medical instrument such as, for example, an endoscope. The covering further comprises means for removing the sheath from the medical instrument.

The medical instrument cover of the present invention is intended to cover a variety of medical instruments to simplify cleaning of said instruments. Exemplary of the medical instruments which are intended to be covered by the cover of the instant application are endoscopes. Those skilled in the art will recognize that the term endoscope refers to an instrument for visualizing the interior to a hollow organ. Specifically, the covering of the present invention is suitable for use on sigmoidoscopes, duodenoscopes, upper G.I. fiberscopes, bronchofiberscopes, colonoscopes and the like. Those skilled in the art will recognize that endoscopes are generally in the shape of tubes or cylinders having a length which is substantially greater than its diameter.

Referring now to the figures, FIG. 1 illustrates a medical instrument cover 10 suitable for use in covering an endoscope. The covering 10 comprises an elongate generally tubular sheath 12 which defines a first open end 14 and a second open end 16. Additionally, the generally tubular sheath 12 defines an interior surface 18. Attached to the interior surface 18 of sheath 12 are means for removing the sheath from the medical instrument. In the illustrated embodiment, the means for removing the sheath comprises a filament 20 attached to the interior surface of the sheath 12. Filament 20 is attached to the interior surface of the sheath 12 at or near the end 16 and extends in the elongate direction towards the end 14. An end portion 22 of the filament 20 extends beyond the opening 14. In use, when the cover 10 is in place about an endoscope, end portion 22 of filament 20 can be grasped and pulled outwardly from sheath 12. In so doing, filament 20 cuts and separates sheath 12 along its length. In this manner, sheath 12 is easily removed from the endoscope.

FIG. 2 illustrates a cross-section of the cover of FIG. 1 taken along line 2—2 of FIG. 1. FIG. 2 again illustrates the cover of FIG. 1 comprising the elongate generally tubular sheath 12 defining two open ends 14, 16 and the interior surface 18. Attached to interior surface 18 is the filament 20. The end portion 22 of the filament 20 extends beyond one end of the sheath 12.

By stating that filament 20 is attached to the interior of sheath 12 it is intended to include those cases wherein filament 20 is attached merely in one location, for example, near end 16, or where filament 20 is attached to the interior surface 18 along its entire length. Additionally, those skilled in the art will recognize that it may be possible to embed the filament 20 within the sheath 12. Accordingly, reference to filament 20 being attached to the interior surface of sheath 12 is also intended to encompass those situations wherein filament 20 is embedded within sheath 12 in such a manner that removal of filament 20 as hereinbefore and hereinafter described separates a sufficient portion of sheath 12 to allow for its easy removal from an endoscope.

Further, while in the illustrated embodiment, means for removing the sheath from the medical instrument comprises filament 20, it is to be understood that any means of removing the sheath is intended to be within the scope of the instant invention. The filament 20 may comprise a thread of a natural or synthetic material, metal or any other suitable substance. It is merely required that the filament 20 possess sufficient structural integrity to be capable of performing in the described manner.

The elongate generally tubular sheath of the present invention is formed from an elastomeric material. By forming the sheath from an elastomeric material, it is possible to ensure a snug and intimate fit of the sheath on the medical instrument. Suitable elastomeric materials include polymeric resinous materials. Examples of suitable polymeric resinous materials are the natural and synthetic rubbers, thermoplastic polymeric materials such as polyethylene, polypropylene, polyurethane, and combinations of natural or synthetic rubbers with thermoplastic polymeric materials such as rubber modified polyethylene, rubber modified polystyrene and the like.

It is desirable to obtain a snug fit when the cover is employed on a medical instrument, such as an endoscope, to ensure that the cover remains in position during use of the endoscope. To ensure that the cover remains in position on the endoscope, it may be desirable to form the end 16 with a slightly smaller diameter than the rest of the sheath. Alternatively, the interior surface 18 proximate end 16 may have mechanical deformations such as bumps and the like that create an uneven surface and thereby increase the adhesion between the cover and the endoscope. Another alternative would be to apply an adhesive to the interior surface 18 in the area of end 16. The adhesive would have sufficient adhesive power to hold the cover in place during use, but would not adhere with such strength as to interfere to an undesirable degree with removal of the cover after use. Suitable adhesives are known to those skilled in the art.

The thickness of the sheath 12 will be selected according to the structural integrity required for the particular medical instrument it is desired to cover and the use to which said covered medical instrument is to be employed. As a general rule, the sheath will be relatively thin. Those skilled in the art will readily appreciate a thickness suitable for a particular covering. For example, when the covering is intended to cover an endoscope, it is believed that a sheath having a thickness of from about 0.002 to about 0.05 inches will be suitable for use.

When the cover is intended for use on an endoscope, the sheath will have a diameter so that the cover fits snugly on the endoscope. Commercially available endoscopes generally have a diameter of from about 1.5 mm to about 15 mm and a length of from about 35 cm to about 200 cm. Accordingly, the sheath will have a diameter somewhat smaller than the diameter of the endoscope to ensure a snug fit. For example, the diameter of the sheath may be from about 1.0 mm to about 15 mm beneficially from about 1.5 mm to about 13 mm. The length of the sheath may vary from about 25 to about 210 cm beneficially from about 30 to about 200 cm.

Referring to FIG. 3, a second embodiment of the present invention is illustrated. FIG. 3 illustrates a sheath 24 defining open ends 26 and 28 and an interior surface 30. Attached to the interior surface 30 of sheath 24 are means 32 and 34 for removing the sheath from a medical instrument. In the illustrated embodiment, means 32 and 34 for removing the sheath from the medical instrument comprise strips of a material, such as cloth, attached to the interior surface 30. Reference to means 32 and 34 being attached to interior surface 30 is intended to include those situations wherein the means 32 and 34 are attached to the interior surface 30 at a single location, along their entire length, or embedded within the sheath 24. End portions 36 and 38 of means 32 and 34, respectively, extend beyond one end of the sheath. In use, means 32 and 34 function by having an end user grab end portions 36 and 38 and pull said end portions toward the opposite end of the sheath. In this manner, the sheath is removed from the medical instrument.

Again, any means capable of removing the sheath from the medical instrument is intended to be within the scope of this invention. In the embodiment illustrated in FIG. 3, the means for removing the sheath comprise strips of cloth. It is to be understood that a single strip of cloth may be employed as well as a single strip of a variety of other materials which possess the structural integrity necessary to function in the described manner.

Referring now to FIG. 4, the medical covering of FIG. 1 is illustrated in place about an endoscope. As can be seen from FIG. 4, the end 16 of the sheath 12 corresponds generally to the end of the endoscope 40. It is noted that a portion of the endoscope is illustrated as extending beyond end 14 of the sheath 12. In order to enable easy operation of the means for removing the sheath, end portion 22 of filament 20 is shown extending beyond the sheath 12 to enable a user to grasp said filament and separate and remove the sheath in the above-described manner.

FIG. 5 illustrates a cross-sectional view of FIG. 4 taken along line 5—5.

A method of using the medical instrument cover of the present invention will now be described. In the illustrated embodiment, the cover is intended for use on an endoscope. In practice, an endoscope is provided. The medical instrument cover of the present invention is then applied to cover at least a portion of the endoscope. It is anticipated that when the cover of the present invention is intended for use on an endoscope, the cover may be provided in a rolled up manner. That is, the cover 10 is rolled upon itself similar to the manner in which condoms are currently supplied. Accordingly, one end of the sheath can be placed on one end of the endoscope and the cover 10 then unrolled to cover a portion of the endoscope. The endoscope is then employed in a medical procedure known to those skilled in the art. After the medical procedure is complete, the sheath can be removed from the endoscope either by separating the sheath and allowing it to peel away from the endoscope or by supplying other means to remove the sheath from the endoscope.

In the illustrated embodiment wherein the covering of the present invention is intended for use on an endoscope, it may be desirable to employ a lubricating agent along the outside of the sheath. Again, those skilled in the art will recognize suitable lubricants as well as means suitable for applying those lubricants to the sheath.

A variety of methods may be employed to form the illustrated endoscope cover. Those skilled in the art will recognize means suitable for forming said cover. Exemplary of one means for forming the illustrated covers would be to provide a mandrel which is dipped in a latex of an elastomeric material and allowed to dry. Subsequent dippings will serve to increase the thickness of the elastomeric material until a desirable thickness is obtained. In this manner a sheath open on one end and closed on the other is formed. The closed end can then be cut off to form a second open end. The sheath can then be rolled upon itself and removed from the mandrel. Similarly, those skilled in the art will recognize a variety of means suitable for attaching the means for removing the sheath to the interior surface of said sheath. For example, the filament 20 may be attached to the mandrel before the mandrel is dipped in a latex of an elastomeric material, as hereinbefore described. After subsequent formation of the sheath is complete, the filament 20 will be adhered to the interior surface of sheath 12 and can be rolled and removed from the mandrel.

Alternatively, if it is desired to embed the filament 20 in the interior of sheath 12, a mandrel can be dipped in a latex, as previously described. After forming a thin layer of elastomeric material, filament 20 can be applied to said layer of elastomeric material and subsequent dippings of the mandrel into a latex conducted to form a layer of sheath material on top of the filament 20. Again, the resultant sheath can be cut and rolled upon itself and removed from the mandrel.

Those skilled in the art will appreciate a number of other methods of manufacturing the medical instrument coverings of the present invention. Obviously, the exact method employed will depend to a certain extent on the medical instrument it is desired to cover.

As is apparent from the foregoing specification, the present invention is capable of being embodied with various alterations and modifications from those described above. For this reason, it is to be fully understood that all of the foregoing is intended to be merely illustrative and is not intended to limit, in any manner, the scope of the invention as set forth in the following claims.

What is claimed is:

1. A medical instrument cover, said cover comprising:
    an elongate generally tubular sheath of an elastomeric material being open at both ends, defining an interior surface and being configured to fit on a medical instrument; and
    means for removing the cover from the medical instrument, wherein the means for removing the cover comprises a filament attached to the interior surface of the sheath and extending along the elongate direction.

2. The medical instrument cover of claim 1 wherein the filament comprises a thread.

3. The medical instrument cover of claim 1 wherein the filament is attached to the interior of the sheath at a location generally near one end of the sheath.

4. The medical instrument cover of claim 1 wherein the filament is attached to the interior of the sheath along substantially the entire length of the sheath.

5. The medical instrument cover of claim 1 wherein a portion of the filament extends beyond one end of the sheath.

6. The medical instrument cover of claim 1 wherein the filament is embedded in the sheath.

7. A medical instrument cover, said cover comprising:
    an elongate generally tubular sheath of an elastomeric material being open at both ends, defining an interior surface and being configured to fit on a medical instrument; and
    means for removing the cover from the medical instrument without touching the sheath,
    wherein the means for removing the cover comprises two strips of material attached to the interior surface of the sheath and extending along its length.

8. A method of employing an endoscope, the steps of the method comprising:
    providing an endoscope;
    applying a cover to the endoscope, said cover comprising:
        an elongate generally tubular sheath of an elastomeric material being open at both ends, defining an interior surface and being configured to fit on a medical instrument; and
        means for removing the cover from the endoscope;
    employing the covered endoscope in a medical procedure; and using the means for removing the cover to remove the cover from the endoscope,
    wherein the means for removing the cover comprises a filament attached to the interior surface of the sheath and extending along the elongate direction and further wherein the cover is removed from the endoscope by using the filament to cut the sheath.

9. A medical instrument cover, said cover comprising:
- an elongate generally tubular sheath of a natural or synthetic rubber, being open on both ends, defining an interior surface and being configured to fit on a medical instrument; and
- a filament embedded in the sheath and extending along substantially the entire length of the sheath in an elongate direction wherein the sheath has a diameter of from about 1.5 mm to about 13 mm and a length of from about 30 cm to about 200 cm.

10. A method of employing an endoscope, the steps of the method comprising:
- providing an endoscope;
- applying a cover to the endoscope, said cover comprising:
  - an elongate generally tubular sheath of an elastomeric material being open at both ends, defining an interior surface and being configured to fit on a medical instrument; and
  - means for removing the cover from the endoscope;
- employing the covered endoscope in a medical procedure; and
- using the means for removing the cover to remove the cover from the endoscope,
- wherein the means for removing the cover comprises a strip of material attached to the sheath and extending along the elongate direction and further wherein the cover is removed from the endoscope by using the strip of material to pull the cover from the endoscope.

11. A medical instrument cover, the cover consisting of:
- an elongate generally tubular sheath of an elastomeric material being open at both ends, defining an interior surface and being configured to fit on a medical instrument; and
- means for removing the cover from the medical instrument,
- wherein the means for removing the cover includes a filament attached to the sheath and extending along the elongate direction.

12. A method of employing an endoscope, the steps of the method comprising:
- providing an endoscope;
- applying a cover to the endoscope, said cover comprising:
  - an elongate generally tubular sheath of an elastomeric material being open at both ends, defining an interior surface and being configured to fit on a medical instrument; and
  - means for removing the cover from the endoscope; employing the covered endoscope in a medical procedure; and using the means for removing the cover to remove the cover from the endoscope,
- wherein the means for removing the cover comprises a strip of material attached to the sheath and extending along the elongate direction and further wherein the cover is removed from the endoscope by using the strip of material to pull the cover from the endoscope.

* * * * *